US010709380B2

(12) United States Patent
Chang et al.

(10) Patent No.: US 10,709,380 B2
(45) Date of Patent: Jul. 14, 2020

(54) METHOD AND APPARATUS FOR PULSE SIGNAL ANALYZING

(71) Applicant: Winbond Electronics Corp., Taichung (TW)

(72) Inventors: Chia-Chi Chang, Taichung (TW); Hung-Yi Hsu, Taichung (TW)

(73) Assignee: Winbond Electronics Corp., Taichung (TW)

( * ) Notice: Subject to any disclaimer, the term of this patent is extended or adjusted under 35 U.S.C. 154(b) by 261 days.

(21) Appl. No.: 15/426,066

(22) Filed: Feb. 7, 2017

(65) Prior Publication Data

US 2018/0055445 A1    Mar. 1, 2018

(30) Foreign Application Priority Data

Aug. 30, 2016  (CN) .......................... 2016 1 0768371

(51) Int. Cl.
*A61B 5/00*    (2006.01)
*A61B 5/024*    (2006.01)
*A61B 5/02*    (2006.01)

(52) U.S. Cl.
CPC ............ *A61B 5/4854* (2013.01); *A61B 5/024* (2013.01); *A61B 5/7253* (2013.01); *A61B 5/7275* (2013.01); *A61B 5/02007* (2013.01); *A61B 5/02416* (2013.01)

(58) Field of Classification Search
CPC ...... A61B 5/4854; A61B 5/024; A61B 5/7275
See application file for complete search history.

(56) References Cited

U.S. PATENT DOCUMENTS

| 5,623,933 A * | 4/1997 | Amano ................ A61B 5/6826 600/500 |
| 2007/0265508 A1 | 11/2007 | Sheikhzadeh-Nadjar et al. |
| 2008/0103398 A1 | 5/2008 | Huang |
| 2009/0124914 A1 | 5/2009 | Kuo et al. |

(Continued)

FOREIGN PATENT DOCUMENTS

| CN | 101036576 | 9/2007 |
| CN | 101668476 | 3/2010 |

(Continued)

OTHER PUBLICATIONS

Omboni, Stefano, et al. "Spectral and sequence analysis of finger blood pressure variability. Comparison with analysis of intra-arterial recordings." Hypertension 22.1 (1993): 26-33. (Year: 1993).*

(Continued)

*Primary Examiner* — David J. McCrosky
(74) *Attorney, Agent, or Firm* — JCIPRNET

(57) ABSTRACT

A method and an apparatus for pulse signal analyzing are provided. The method includes: receiving a pulse signal; decomposing the pulse signal into a plurality of characteristics signal; generating a spectrum for each of the plurality of characteristics signal by using a spectrum projection; obtaining a plurality of quantized data for each of the plurality of characteristics signal by quantizing the spectrum corresponding to each of the plurality of characteristics signal; and determining a physiological condition corresponding to the pulse signal according to the plurality of quantized data of the plurality of characteristics signal.

8 Claims, 5 Drawing Sheets

(56) References Cited

U.S. PATENT DOCUMENTS

2015/0018631 A1 1/2015 Lee
2015/0223711 A1 8/2015 Raeder et al.

FOREIGN PATENT DOCUMENTS

| CN | 103027668 | 4/2013 | | |
|----|-----------|--------|---|---|
| CN | 103049631 | 4/2013 | | |
| CN | 103400069 | 11/2013 | | |
| EP | 1419730 | 5/2004 | | |
| EP | 1982646 A2 * | 10/2008 | ........... | A61B 5/4854 |
| GB | 1383958 | 2/1974 | | |
| JP | H06197871 | 7/1994 | | |
| JP | 2011212364 | 10/2011 | | |
| JP | 2014193349 | 10/2014 | | |
| JP | 2015016268 | 1/2015 | | |
| JP | 2016538005 | 12/2016 | | |
| JP | 2016539718 | 12/2016 | | |
| TW | I259073 | 8/2006 | | |
| TW | 200841860 | 11/2008 | | |
| TW | I330073 | 9/2010 | | |
| TW | 201521683 | 6/2015 | | |

OTHER PUBLICATIONS

Sherebrin, M. H., et al. "Frequency analysis of the peripheral pulse wave detected in the finger with a photoplethysmograph." IEEE Transactions on biomedical engineering 37.3 (1990): 313-317. (Year: 1990).*

Japanese Office Action for corresponding application, Machine Translation, dated Oct. 2018 (Year: 2018).*

Japanese Office Action for corresponding application, Machine Translation, dated Feb. 2018 (Year: 2018).*

"Office Action of Japan Counterpart Application", dated Feb. 20, 2018, p. 1-p. 4.

Chen et al., "Ensemble Empirical Mode Decomposition for atherosclerosis in high-risk subjects," 8th International Conference on Information, Communications and Signal Processing (ICICS), Dec. 13-16, 2011, pp. 1-4.

Pan Liu et al., "Pulse Condition Signal Reconstruction Based on EEMD Decomposition and Classification Applications Thereof," with (partial) English translation thereof, The 15th Annual Conference of TCM Diagnosis of TCM Diagnostics Branch of China Association of Chinese Medicine, Jul. 18, 2014, pp. 224-228.

* cited by examiner

METHOD AND APPARATUS FOR PULSE SIGNAL ANALYZING

CROSS-REFERENCE TO RELATED APPLICATION

This application claims the priority benefit of China application serial no. 201610768371.3, filed on Aug. 30, 2016. The entirety of the above-mentioned patent application is hereby incorporated by reference herein and made a part of this specification.

BACKGROUND OF THE INVENTION

Field of the Invention

The invention relates to a method and an apparatus for pulse signal analyzing for traditional Chinese medicine.

Description of Related Art

In today's medical care system, the main emphasis is on precise medical care and personal care. One of the key techniques is clinical quantitative indicators for diagnostic reference, and the specificity, sensitivity and reliability of the indicators often depend on calculation formulas and calculation methods thereof. In non-invasive clinical monitoring of a cardiovascular system, in the past, clinical evidence of western medicine is generally adopted for corresponding to a physiological significance of the indicator, though in pulse diagnosis of traditional Chinese medicine (TCM), there are less corresponding quantitative calculus techniques.

An analysis technique of general pulse diagnosis monitors generally adopts linear frequency division (for example, Fourier transform) or timing characteristics analysis (for example, wavelet transform) to implement quantization and indicator calculation of pulse waveforms, and a part of the pulse diagnosis monitors even adopts pulse rate variability frequency domain quantization characteristics used for evaluating an autonomic nervous function in the western medicine as a reference display indicator of the pulse diagnosis monitor. However, compared to the conventional analysis techniques, it is hard to reflect pulse characteristics used by the TCM doctors in traditional pulse diagnosis, and the pulse characteristics contain a magnitude variation in space (Chon, Gwan and Check) and time (floating, moderate, sinking).

SUMMARY OF THE INVENTION

The invention is directed to a method and an apparatus for pulse signal analyzing, which may effectively reflect a magnitude variation of space (Chon, Gwan and Check) and time (floating, moderate, sinking) in traditional Chinese medicine (TCM) pulse diagnosis, and are effectively applied to the TCM pulse diagnosis or personal health care, etc.

The invention provides a method for pulse signal analysing, which includes following steps: receiving a pulse signal; decomposing the pulse signal into a plurality of characteristics signals; performing a spectrum projection to each of the characteristics signals to generate a spectrum; obtaining a plurality of quantized data corresponding to each of the characteristics signals by quantizing the spectrum corresponding to each of the characteristics signals; and determining a physiological condition corresponding to the pulse signal according to the plurality of quantized data corresponding to the characteristics signals.

In an embodiment of the invention, the characteristics signals are combined to form the pulse signal.

In an embodiment of the invention, the characteristics signals respectively correspond to a physiological significance.

In an embodiment of the invention, the step of obtaining a plurality of the quantized data corresponding to each of the characteristics signals by quantizing the spectrum corresponding to each of the characteristics signals includes calculating an energy density and an average period corresponding to each of the characteristics signals according to the spectrum corresponding to each of the characteristics signals.

In an embodiment of the invention, the step of determining the physiological condition corresponding to the pulse signal according to the plurality of quantized data corresponding to the characteristics signals includes comparing the quantized data corresponding to each of the characteristics signals with reference data to determine the physiological condition corresponding to the pulse signal.

In an embodiment of the invention, the physiological condition at least includes one of a plurality of TCM pulse conditions.

The invention provides a pulse signal analyzing device including a processing unit, and the processing unit is configured to receive a pulse signal, decompose the pulse signal into a plurality of characteristics signals, perform a spectrum projection to each of the characteristics signals to generate a spectrum, obtain a plurality of quantized data corresponding to each of the characteristics signals by quantizing the spectrum corresponding to each of the characteristics signals, and determine a physiological condition corresponding to the pulse signal according to the plurality of quantized data corresponding to the characteristics signals.

In an embodiment of the invention, the characteristics signals are combined to form the pulse signal.

In an embodiment of the invention, the characteristics signals respectively correspond to a physiological significance.

In an embodiment of the invention, in the operation of obtaining a plurality of the quantized data corresponding to each of the characteristics signals by quantizing the spectrum corresponding to each of the characteristics signals, the processing unit further calculates an energy density and an average period corresponding to each of the characteristics signals according to the spectrum corresponding to each of the characteristics signals.

In an embodiment of the invention, in the operation of determining the physiological condition corresponding to the pulse signal according to the plurality of quantized data corresponding to the characteristics signals, the processing unit further compares the quantized data corresponding to each of the characteristics signals with reference data to determine the physiological condition corresponding to the pulse signal.

In an embodiment of the invention, the physiological condition at least includes one of a plurality of TCM pulse conditions.

According to the above description, the pulse signal can be decomposed into a plurality of characteristics signals having physiological significances, and spectrum projection and quantization are performed to each of the characteristics signals to obtain a plurality of quantized data, and finally the TCM pulse condition corresponding to the pulse signal is determined according to the quantized data corresponding to the characteristics signals. In this way, a magnitude variation related to space (Chon, Gwan and Check) and time (floating, moderate, sinking) in TCM pulse diagnosis can be effectively presented, and the method and the apparatus for pulse signal analyzing can be effectively applied to the TCM pulse diagnosis or personal health care, etc.

In order to make the aforementioned and other characteristics and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
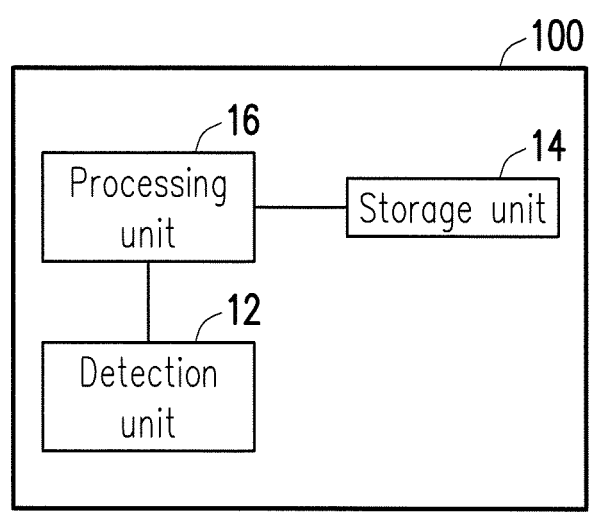
FIG. 1 is a block diagram of a pulse signal analyzing device according to an embodiment of the invention.

FIG. 1 is a block diagram of a pulse signal analyzing device according to an embodiment of the invention. Referring to FIG. 1, the pulse signal analyzing device 100 of the present embodiment includes a detection unit 12, a storage unit 14 and a processing unit 16. The pulse signal analyzing device 100 is, for example, an electronic device such as a mobile phone, a tablet personal computer, a notebook, or a general desktop computer, etc., which is not limited by the invention.

The detection unit 12 can be used for detecting a pulse of a user to generate a corresponding pulse signal. The detection unit 12 is, for example, a pulse oximetry, though the invention is not limited thereto, and the detection unit 12 can also be a detector using optical, ultrasonic wave, pressure or other method to obtain the pulse signal. Moreover, the detection unit 12 may also measure the pulse of the user through a finger, an arm, an ear or other body part of the user to obtain the pulse signal. It should be noted that in the present exemplary embodiment, the detection unit 12 is included in the pulse signal analyzing device 100. However, in another exemplary embodiment, the pulse signal analyzing device 100 may not include the detection unit 12, and the detection unit can be connected to the pulse signal analyzing device 100 through an external manner.

The storage unit 14 can be any type of a fixed or movable random access memory (RAM), a read-only memory (ROM), a flash memory or a similar device or a combination of the aforementioned devices. In the present embodiment, the storage unit 14 is used for recording a plurality of modules executing the method for pulse signal analyzing of the invention. These modules are, for example, a plurality of program codes stored in the storage unit 14, which can be loaded into the processing unit 16 of the pulse signal analyzing device 100, and the processing unit 16 executes the method for pulse signal analyzing of the invention.

The processing unit 16 is respectively connected to the detection unit 12 and the storage unit 14, and the processing unit 16 can be a central processing unit (CPU), or other programmable general purpose or special purpose microprocessor, a digital signal processor (DSP), a programmable controller, and application specific integrated circuit (ASIC) or other similar device or a combination of the aforementioned devices. In the present embodiment, the processing unit 16 is used for accessing and executing the modules recorded in the storage unit 14, so as to execute the method for pulse signal analyzing of the invention.

It should be noted that in the present exemplary embodiment, the method for pulse signal analyzing is loaded and executed by using program codes. However, in another exemplary embodiment of the invention, the method for pulse signal analyzing of the invention can also be implemented through a hardware circuit, which is not limited by the invention.

FIG. 2A to FIG. 2D are schematic diagrams of the method for pulse signal analyzing according to an embodiment of the invention. The method of the present embodiment is adapted to the aforementioned pulse signal analyzing device 100. A detailed flow of the method of the present embodiment is described below with reference of various components of the pulse signal analyzing device 100 of FIG. 1.

Figure 2A:
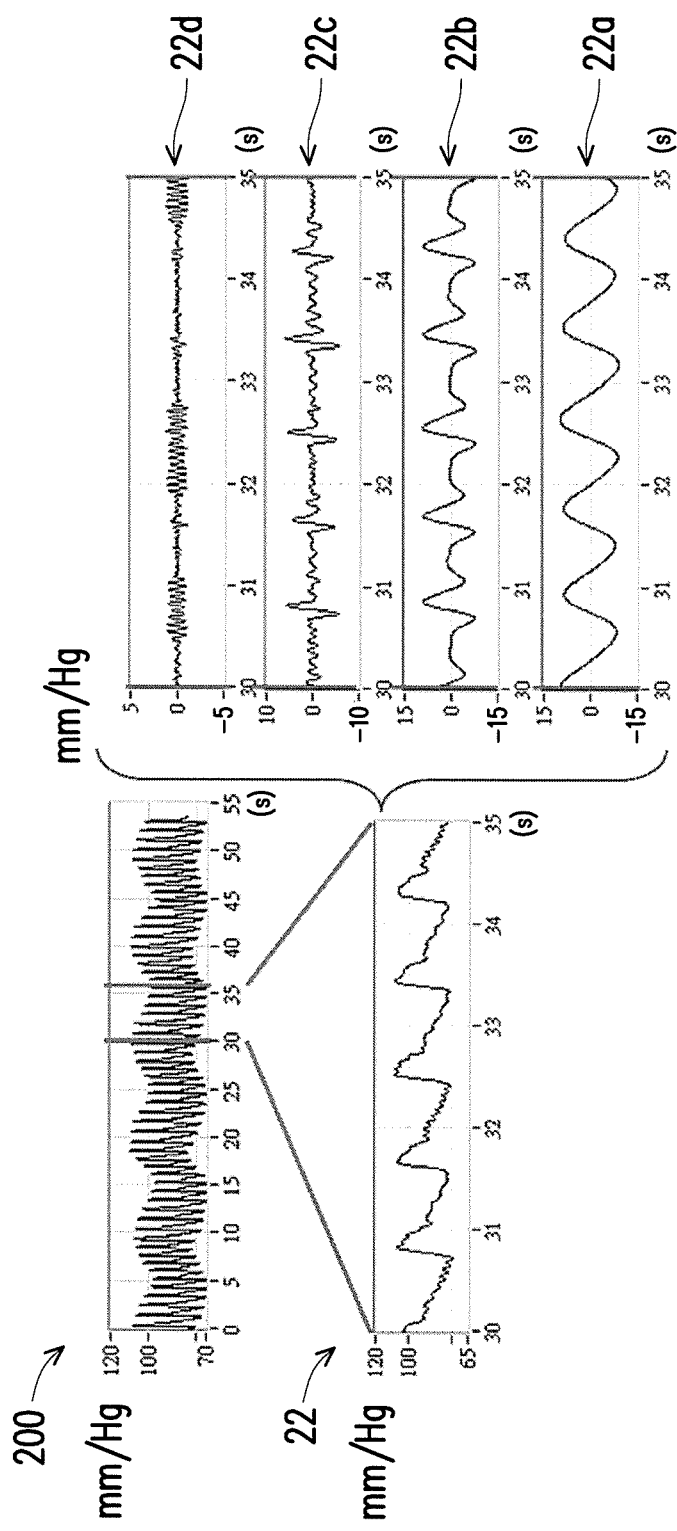
FIG. 2A to FIG. 2D are schematic diagrams of a method for pulse signal analyzing according to an embodiment of the invention.
Figure 2B:
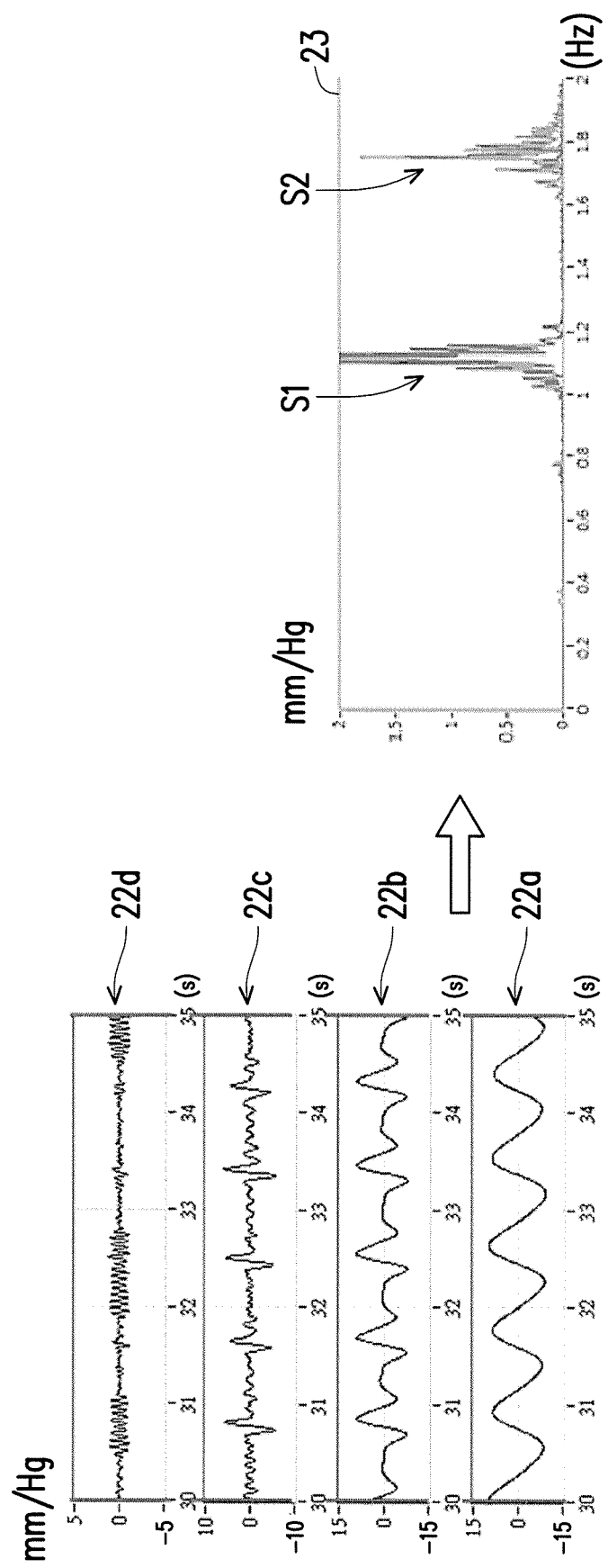

Referring to FIG. 2A, first, the detection unit 12 detects pulses of a user within a period of time to generate a pulse signal 200, and the processing unit 16 receives the pulse signal 200 from the detection unit 12. After the processing unit 16 receives the pulse signal 200 from the detection unit 12, the processing unit 16 decomposes the pulse signal 200 into a plurality of characteristics signals.

For example, the pulse signal 200 in FIG. 2A records the pulses of the user within a period of time (i.e. 0-55 seconds). For simplicity's sake, it is assumed that the processing unit 16 analyzes a pulse signal 22 of a specific time interval (for example, 30-35 seconds) in the pulse signal 200. The processing unit 16 may decompose the pulse signal 22 into a plurality of characteristics signals $22a$-$22d$ according to a non-steady state decomposition method. The non-steady state decomposition method is, for example, an ensemble empirical mode decomposition (EEMD), complementary ensemble empirical mode decomposition (CEEMD), etc., which is not limited by the invention. Particularly, in the present embodiment, since non-steady state decomposition is performed to the pulse signal 22, and the characteristics signals $22a$-$22d$ generated through the non-steady state decomposition can be combined (or recombined) into the pulse signal 22 without distortion.

It should be noted that in the exemplary embodiment of the invention, the non-steady state decomposition method used for decomposing the pulse signal 22 can be determined through the way of clinical experiments, such that the decomposed characteristics signals $22a$-$22d$ respectively correspond to one physiological significance (which is also referred to as clinical significance) of the user. For example, in the present exemplary embodiment, the characteristics signal $22a$ relates to a heart rate of the user. The characteristics signal $22b$ relates to pressure rebound of vascular branching when the heart output blood. The characteristics signal $22c$ relates to a reaction of the surrounding tissues. The characteristics signal $22d$ relates to a high frequency noise of the detector. However, it should be noted that the number of the decomposed characteristics signals and the biological significance corresponding to each of the characteristics signals are not limited by the invention.

Then, the processing unit 16 performs a spectrum projection to each of the characteristics signals $22a$-$22d$ to individually generate a spectrum. In detail, referring to FIG.

2B, the processing unit 16 may perform the spectrum projection to the characteristics signal 22a to generate a spectrum S1, and the processing unit 16 may perform the spectrum projection to the characteristics signal 22b to generate a spectrum S2. It should be noted that although a spectrum diagram 23 of FIG. 2B only illustrates the spectrum S1 corresponding to the characteristics signal 22a and the spectrum S2 corresponding to the characteristics signal 22b, it should be noted that a spectrum S3 (not shown) corresponding to the characteristics signal 22c and a spectrum S4 (not shown) corresponding to the characteristics signal 22d are respectively within a range greater than a frequency of 2 Hz in the spectrum diagram 23 (i.e. a right side of the spectrum S2). Moreover, in the conventional technique, there are a plurality of methods for projecting the characteristics signal to generate the spectrum, for example, a fast Fourier transform (FFT) method or a discrete wavelet transform (DWT) method, etc., which are not repeated.

Figure 2C:
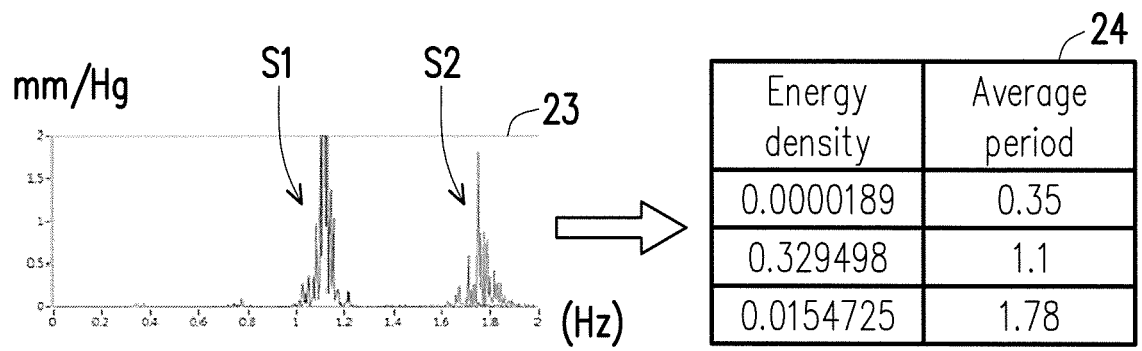

Then, referring to FIG. 2C, the processing unit 16 quantizes the spectrums S1-S4 corresponding to each of the characteristics signals 22a-22d to obtain a plurality of quantized data (for example, a quantized data table 24 of FIG. 2C) corresponding to each of the characteristics signals 22a-22d. The processing unit 16 may calculate an energy density and an average period corresponding to each of the characteristics signals 22a-22d according to the spectrums S1-S4 corresponding to each of the characteristics signals 22a-22d. It should be noted that the quantized data table 24 only schematically lists corresponding relationships of three groups of energy densities and average periods, though the quantized data table 24 can be used to record the energy density and the average period corresponding to each of the characteristics signals 22a-22d.

In detail, the processing unit 16 respectively calculates the energy densities and the average periods of the spectrum S1 corresponding to the characteristics signal 22a, the spectrum S2 corresponding to the characteristics signal 22b, the spectrum S3 corresponding to the characteristics signal 22c and the spectrum S4 corresponding to the characteristics signal 22d. The equation of the energy density is as follows:

$$E_n = \frac{1}{N} \sum_{t=1}^{N} [IMF_n(t)]^2 \qquad (1)$$

Where, n represents a specific spectrum. For example, in the present exemplary embodiment, when n=1, $E_1$ represents the energy density of the spectrum S1; and when n=2, $E_2$ represents the energy density of the spectrum S2, and the others are deduced by analogy. N represents a total number of time points in the specific spectrum n, where each of the time points can be obtained through reciprocals of frequencies (for example, each value on a horizontal axis of the spectrum diagram 23). $IMF_n(t)$ represents energy intensity corresponding to a time point t within a time range of a certain specific spectrum n. For example, $IMF_1(t)$ represents the energy intensity of a first time point in the spectrum S1; $IMF_2(t)$ represents the energy intensity of an $N^{th}$ time point in the spectrum S2, and the others are deduced by analogy.

According to the equation (1), the processing unit 16 may respectively calculate an energy density $E_1$ of the spectrum S1 corresponding to the characteristics signal 22a, an energy density $E_2$ of the spectrum S2 corresponding to the characteristics signal 22b, an energy density $E_3$ of the spectrum S3 corresponding to the characteristics signal 22c, and an energy density $E_4$ of the spectrum S4 corresponding to the characteristics signal 22d. The energy density can be used to represent the energy intensity of a main frequency in the corresponding spectrum, where the main frequency refers to a frequency corresponding to a peak value of the spectrum. Moreover, in the TCM pulse diagnosis, floating, moderate, sinking represents variations of depth and strength of the pulse, and in the present exemplary embodiment, since the processing unit 16 has decomposed the pulse signal 22 into the characteristics signals 22a-22d, and the characteristics signals 22a-22d respectively correspond to a physiological significance of the user, the energy densities $E_1$-$E_4$ respectively corresponding to the characteristics signals 22a-22d can be used to analyse the variations related to the floating, moderate, sinking in the TCM pulse diagnosis.

Moreover, the equation of the average period is as follows:

$$\overline{T_n} = \int S_{lnT,n} d\ln T \left( \int S_{lnT,n} \frac{d\ln T}{T} \right)^{-1} \qquad (2)$$

Where, n represents a specific spectrum. For example, in the present exemplary embodiment, when n=1, $\overline{T_1}$ represents the average period of the spectrum S1; when n=2, $\overline{T_2}$ represents the average period of the spectrum S2, and the others are deduced by analogy. Moreover, T represents time, and $S_{ln\,T,n}$ represents a function of natural logarithm of the spectrum n and the time T.

According to the equation (2), the average period $\overline{T_1}$ of the spectrum S1 corresponding to the characteristics signal 22a, the average period $\overline{T_2}$ of the spectrum S2 corresponding to the characteristics signal 22b, the average period $\overline{T_3}$ of the spectrum S3 corresponding to the characteristics signal 22c, and the average period $\overline{T_4}$ of the spectrum S4 corresponding to the characteristics signal 22d can be respectively calculated. The each of the calculated average periods $\overline{T_1}$-$\overline{T_4}$ may respectively represent a period of the main frequency in each of the spectrums S1-S4, and the frequency of the main frequency in each of the spectrums S1-S4 can be obtained by obtaining a reciprocal thereof. Moreover, in the TCM pulse diagnosis, Chon, Gwan and Check represents waveform variations of the pulse in space, and in the present exemplary embodiment, the variations related to the Chon, Gwan and Check in the TCM pulse diagnosis can be analysed according to the relationship of the average periods $\overline{T_1}$-$\overline{T_4}$ and the energy densities $E_1$-$E_4$ corresponding to the characteristics signals 22a-22d.

Figure 2D:
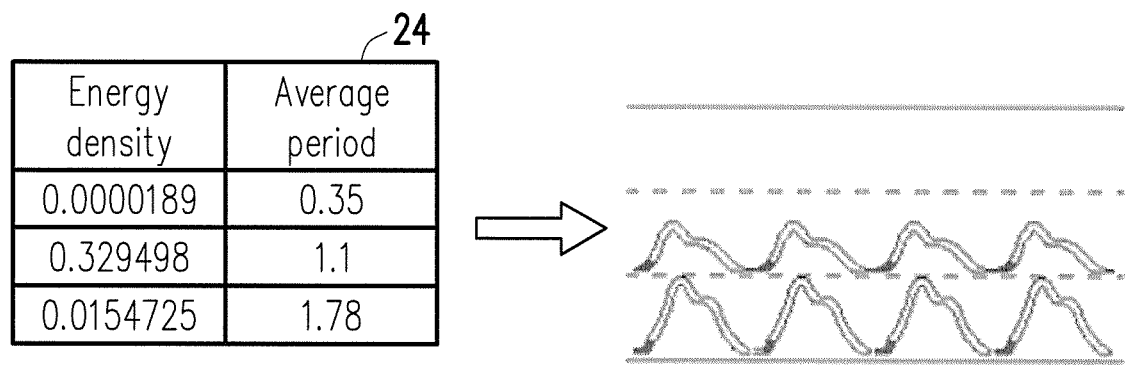

Then, as shown in FIG. 2D, in the present exemplary embodiment, the processing unit 16 determines a physiological condition corresponding to the pulse signal 22 according to the plurality of quantized data (i.e. the energy densities $E_1$-$E_4$ and the average periods $\overline{T_1}$-$\overline{T_4}$) corresponding to the characteristics signals 22a-22d, where the physiological condition at least includes one of a plurality of TCM pulse conditions, for example, sthenia pulse, asthenia pulse, etc. To be specific, in the present exemplary embodiment, a database can be preset in the storage unit 14, where the database stores a plurality of reference data, and the reference data represents corresponding relationships between the combinations of the average periods and the energy densities and a plurality of TCM pulse conditions, where the corresponding relationships can be obtained through clinical experiments. The processing unit 16 may compare the quantized data (i.e. the energy densities $E_1$-$E_4$ and the average periods $\overline{T_1}$-$\overline{T_4}$) corresponding to each of the characteristics signals 22a-22d with the reference data to determine the physiological condition corresponding to the pulse signal 22. The processing unit 16 may output a comparison result through an output unit such as a screen, etc., so as to provide a TCM doctor with pulse diagnosis information in traditional pulse diagnosis. Namely, the energy densities $E_1$-$E_4$ and the average periods $\overline{T_1}$-$\overline{T_4}$ respectively corresponding to each of the characteristics signals 22a-22d can be used to reflect the physiological condition of the pulse signal 22, and may correspond to one of a plurality of TCM conditions.

Figure 3:
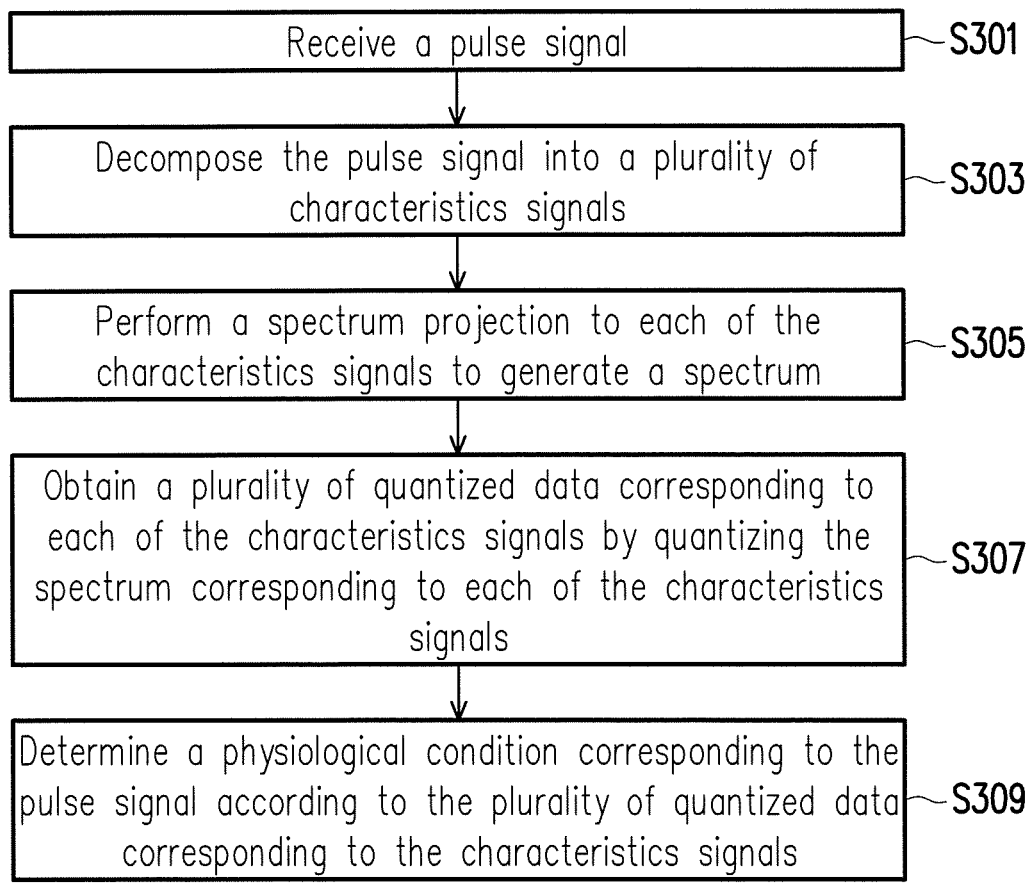
FIG. 3 is a flowchart illustrating a method for pulse signal analysing according to an embodiment of the invention.

FIG. 3 is a flowchart illustrating a method for pulse signal analysing according to an embodiment of the invention.

Referring to FIG. 3, in step S301, the processing unit 16 receives a pulse signal. In step S303, the processing unit 16 decomposes the pulse signal into a plurality of characteristics signals. In step S305, the processing unit 16 perform is a spectrum projection to each of the characteristics signals to generate a spectrum. In step S307, the processing unit 16 obtains a plurality of quantized data corresponding to each of the characteristics signals by quantizing the spectrum corresponding to each of the characteristics signals. Finally, in step S309, the processing unit 16 determines a physiological condition corresponding to the pulse signal according to the plurality of quantized data corresponding to the characteristics signals.

In summary, the pulse signal can be decomposed into a plurality of characteristics signals having physiological significances, and spectrum projection and quantization are performed to each of the characteristics signals to obtain a plurality of quantized data, and finally the TCM pulse condition corresponding to the pulse signal is determined according to the quantized data corresponding to the characteristics signals. In this way, a magnitude variation related to space (Chon, Gwan and Check) and time (floating, moderate, sinking) in the TCM pulse diagnosis can be effectively presented, and characteristics indicators referred by the pulse diagnosis can be effectively presented through the quantization method.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A method for pulse signal analysing, performed by a pulse signal analyzing device comprising a processing unit, the method comprising:
   detecting a pulse signal within a period of time by a detection unit;
   receiving, by the processing unit, the pulse signal;
   decomposing, by the processing unit, the pulse signal into a plurality of characteristics signals;
   performing, by the processing unit, a spectrum projection to each of the characteristics signals to generate a spectrum;
   obtaining, by the processing unit, a plurality of quantized data corresponding to each of the characteristics signals by quantizing the spectrum corresponding to each of the characteristics signals,
   wherein the plurality of quantized data comprise an energy density and an average period corresponding to each of the characteristics signals, and calculates an energy density and the average period of the spectrum corresponding to each of the characteristics signals, the energy density corresponding to a specific spectrum is obtained according to a total number of time points in the specific spectrum, an energy intensity corresponding to a time point within a time range of the specific spectrum,
   wherein an average period corresponding to the specific spectrum is obtained according to a time, a function of natural logarithm of the specific spectrum and the time,
   determining, by the processing unit, a physiological condition corresponding to the pulse signal according to the plurality of quantized data corresponding to the characteristics signals;
   comparing, by the processing unit, the quantized data corresponding to each of the characteristics signals with reference data to determine the physiological condition corresponding to the pulse signal and generates a comparison result;
   outputting, by the processing unit, the physiological condition corresponding to the pulse signal based on the comparison result.

2. The method for pulse signal analysing as claimed in claim 1, wherein the characteristics signals are combined to form the pulse signal.

3. The method for pulse signal analysing as claimed in claim 1, wherein the characteristics signals respectively correspond to a physiological significance.

4. The method for pulse signal analysing as claimed in claim 1, wherein the physiological condition at least comprises one of a plurality of traditional Chinese medicine pulse conditions.

5. A pulse signal analyzing device, comprising:
   a detection unit, configured to detect a pulse signal within a period of time; and
   a processing unit, wherein
   the processing unit is configured to receive the pulse signal,
   the processing unit is configured to decompose the pulse signal into a plurality of characteristics signals,
   the processing unit is configured to perform a spectrum projection to each of the characteristics signals to generate a spectrum,
   the processing unit is configured to obtain a plurality of quantized data corresponding to each of the characteristics signals by quantizing the spectrum corresponding to each of the characteristics signals,
   wherein the plurality of quantized data comprise an energy density and an average period corresponding to each of the characteristics signals, and calculates an energy density and the average period of the spectrum corresponding to each of the characteristics signals, the energy density corresponding to a specific spectrum is obtained according to a total number of time points in the specific spectrum, an energy intensity corresponding to a time point within a time range of the specific spectrum,
   wherein an average period corresponding to the specific spectrum is obtained according to a time, a function of natural logarithm of the specific spectrum and the time,
   the processing unit is configured to determine a physiological condition corresponding to the pulse signal according to the plurality of quantized data corresponding to the characteristics signals,
   the processing unit is configured to compare the quantized data corresponding to each of the characteristics signals with reference data to determine the physiological condition corresponding to the pulse signal and generates a comparison result, and the processing unit is configured to output the physiological condition corresponding to the pulse signal based on the comparison result.

6. The pulse signal analyzing device as claimed in claim 5, wherein the characteristics signals are combined to form the pulse signal.

7. The pulse signal analyzing device as claimed in claim 5, wherein the characteristics signals respectively correspond to a physiological significance.

8. The pulse signal analyzing device as claimed in claim 5, wherein the physiological condition at least comprises one of a plurality of traditional Chinese medicine pulse conditions.

\* \* \* \* \*